Figure 1:
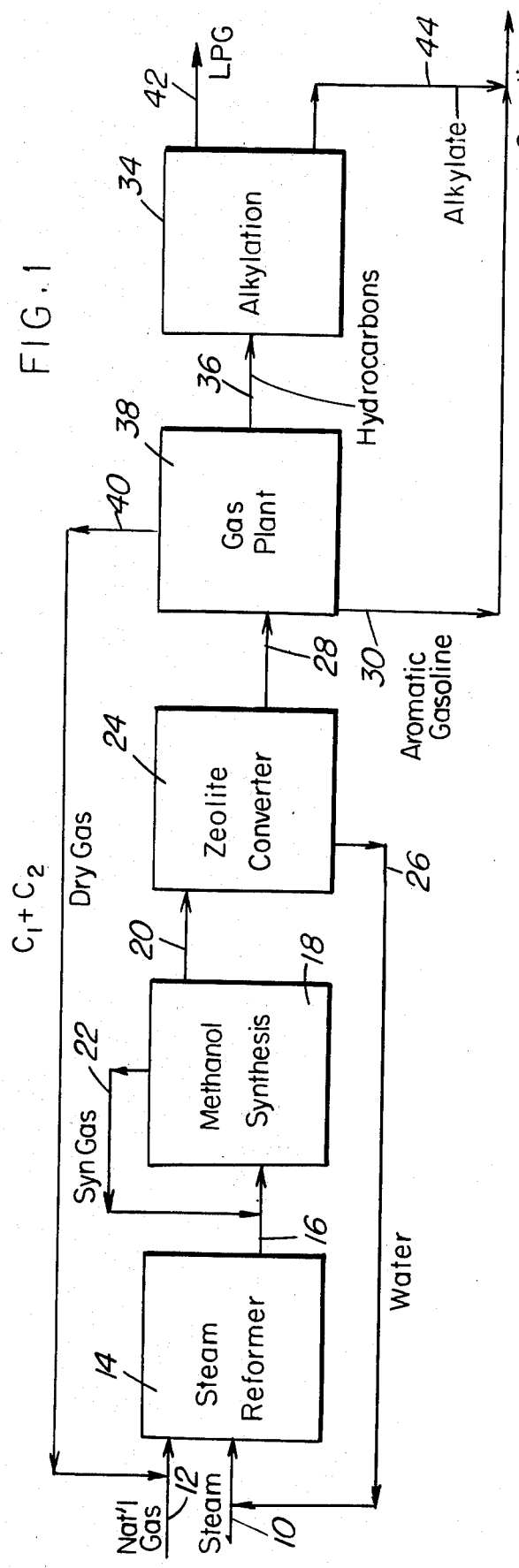

United States Patent [19]

Garwood et al.

[11] 4,048,250

[45] Sept. 13, 1977

[54] CONVERSION OF NATURAL GAS TO GASOLINE AND LPG

[75] Inventors: William E. Garwood, Haddonfield; Solomon M. Jacob; James C. Kuo, both of Cherry Hill, all of N.J.; John J. Wise, Media, Pa.

[73] Assignee: Mobil Oil Corporation, New York, N.Y.

[21] Appl. No.: 566,168

[22] Filed: Apr. 8, 1975

[51] Int. Cl.$^2$ .......................... C07C 3/52; C07C 3/54
[52] U.S. Cl. ............................ 260/683.43; 260/450
[58] Field of Search ............... 44/80; 260/449, 683.42, 260/450, 683.43, 676 R

[56] References Cited

U.S. PATENT DOCUMENTS

| | | | |
|---|---|---|---|
| 2,305,026 | 12/1942 | Munday ............................... | 44/80 |
| 2,683,152 | 7/1954 | Dickinson ........................ | 260/449 R |
| 2,758,960 | 8/1956 | Kelly et al. ......................... | 44/80 |
| 3,251,902 | 5/1966 | Garwood et al. ............... | 260/683.43 |
| 3,541,180 | 11/1970 | Thomas ............................ | 260/683.43 |
| 3,686,354 | 8/1972 | Hervert ............................ | 260/683.43 |
| 3,840,613 | 10/1974 | Eberly, Jr. et al. ............. | 260/683.43 |

*Primary Examiner*—Daniel E. Wyman
*Assistant Examiner*—Mrs. Y. Harris-Smith
*Attorney, Agent, or Firm*—Charles A. Huggett; Michael G. Gilman

[57] ABSTRACT

Natural gas is steam reformed to a mixture of carbon monoxide, carbon dioxide and hydrogen which mixture is converted, over a methanol synthesis catalyst, to a mixture of methanol, carbon oxides and hydrogen which methanol is converted to $C_5+$ hydrocarbon gasoline, light gas and water, the water is separated out and may be recycled as steam, the portion of the hydrocarbon fraction which comprises light olefins and isobutane is subjected to acid alkylation to product very high octane hydrocarbon gasoline which is admixed with the $C_5+$ hydrocarbon gasoline from the methanol conversion. The light fuel gas ($C_1$ to $C_2$) produced in the methanol conversion is recycled to the steam reformer and the LPG ($C_3 + C_4$) produced therein is recovered and sold.

10 Claims, 2 Drawing Figures

CONVERSION OF NATURAL GAS TO GASOLINE AND LPG

This invention relates to the upgrading of natural gas. It more particularly refers to a novel process for converting natural gas to high octane hydrocarbon gasoline.

With the current shortages in petroleum in many of the industrialized areas of the world, substantial emphasis has been given to utilizing alternative fuel sources. For some purposes, notably operating internal combustion motor vehicles, neither coal nor natural gas are suitable replacement fuels for liquid gasoline. Thus, increased emphasis has recently been placed on such processes as Fischer-Tropsch synthesis for converting these non-liquid fossil fuels to liquid gasoline products. Conventional Fischer-Tropsch technology is capable of converting natural gas to gasoline but it is of relatively low octane number and is not readily reformable to better quality gasoline.

More recently there has been developed new technology for converting methanol and/or other relatively common heterogeneous organic compounds directly to high octane, high quality gasoline. In this respect it is a competitor of conventional Fischer-Tropsch technology in that the methanol or other suitable organic feeds are usually industrially derived from synthesis gas which is in turn derived from natural gas or perhaps coal. Therefore, there has recently been developed a novel process for converting fossil fuels such as coal or natural gas to high quality gasoline via an intermediate comprising methanol. It is desirable to improve this process so as to increase the proportion of non-liquid fossil fuel feed which is converted by the process to more valuable products, namely high octane gasoline and liquifiable petroleum gas (LPG).

Still more recently there have been developed remarkable improvements in technology related to Fischer-Tropsch type conversions. This improved technology relies upon certain novel catalyst compositions which comprise mixtures of components which seem to act synergistically with respect to each other in converting synthesis gas, i.e. mixtures of carbon monoxide and hydrogen, directly to high octane aromatic gasoline. These novel composite catalysts have a carbon monoxide reduction component such as iron, thorium, cobalt, ruthenium, etc. and a zeolite component, particularly a special zeolite of high silica to alumina ratio as will be more particularly defined and detailed below.

It is therefore an object of this invention to provide a novel and improved process for converting fossil fuel to gasoline.

It is another object of this invention to modify such process in a manner such as to maximize high octane gasoline production.

Other and additional objects of this invention will be apparent from a consideration of this entire specification including the claims and the drawing.

Figure 2:
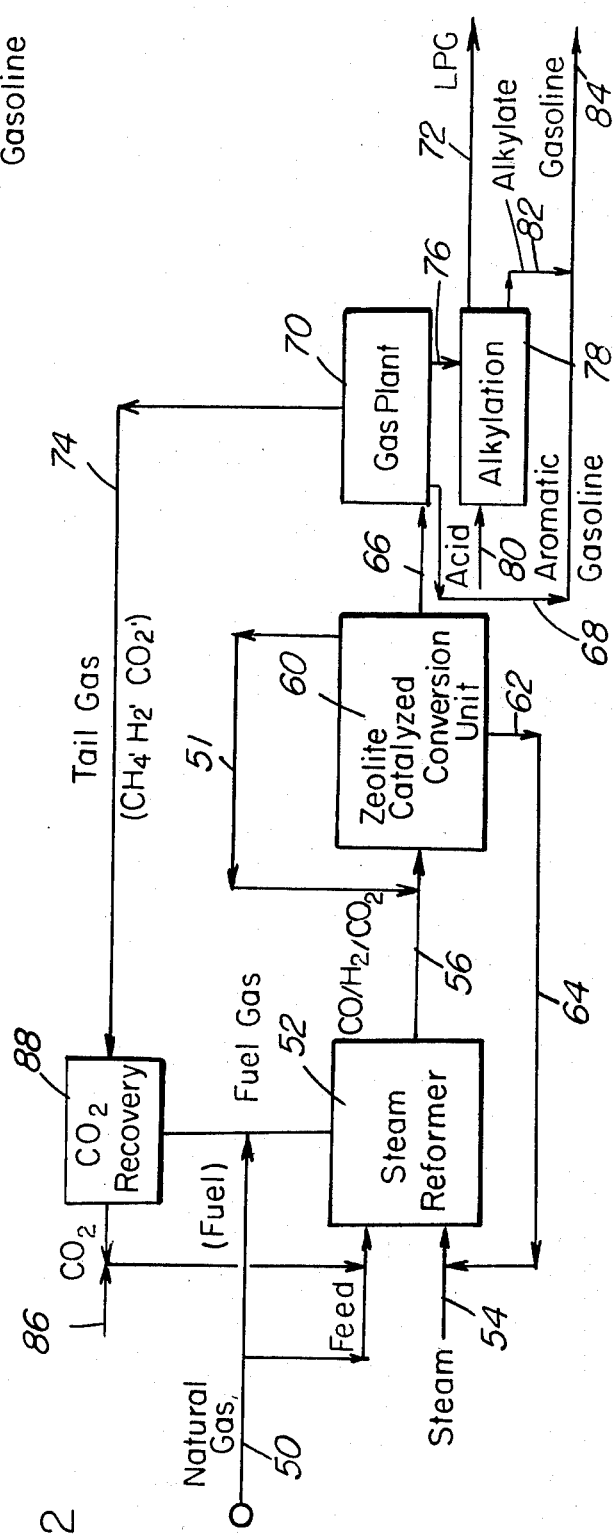

Understanding of this invention will be facilitated by reference to the accompanying drawing in which FIG. 1 is a block flow diagram of one embodiment of this invention; and FIG. 2 is a block flow diagram of a different embodiment of this invention.

In accord with and fulfilling these objects, one aspect of this invention resides in a process comprising steam reforming natural gas, or another mixture of light hydrocarbons, to a gas product comprising carbon monoxide and hydrogen. This gas product may contain carbon dioxide which may be introduced as a result of a water gas shift reaction used to adjust the hydrogen to carbon monoxide ratio or it may be introduced from flue gases or as a recycle stream. However it is introduced, it is an important aspect of this invention that it be present since the ratio of hydrogen to carbon in natural or other gas feeds approaches or is equal to about 4 to 1 whereas the product desirably produced by this product, that is high octane aromatic gasoline, has a ratio of hydrogen to carbon of about 2 to 1. Thus, it is desirable to add carbon or at least conserve carbon in a conversion system which utilizes gas as a feed. According to this invention, the synthesis gas so produced in the reformer, or in an equivalent partial oxidation process, should have a ratio of hydrogen to carbon monoxide of about 1 to 5 to 1 and a ratio of carbon monoxide to carbon dioxide of about 1 to 4 to 1. The synthesis gas producing process is itself per se known. There are several commercially available processes which can readily perform this function. They operate at about 1400° to 1800° F at about 100 to 500 psig and may be catalytic or not. This process is not per se inventive here. Any such process which will produce a synthesis gas as defined above is acceptable for use in this invention.

The second step in the instant process provides for the conversion of the above recited synthesis gas into water and a hydrocarbon product comprising highly aromatic, high octane gasoline. This can be accomplished by one of two techniques or some combination thereof.

In one embodiment of this invention, the synthesis gas is fed to a methanol synthesis process where some portion of it, depending upon the thermodynamic equilibria and exact processing conditions, is converted to methanol and/or dimethyl ether and/or higher alcohols and/or their corresponding ethers or mixtures thereof. The product of the methanol synthesis step may be conveniently broken up into an organic oxygenate portion comprising methanol, and an inorganic portion comprising carbon monoxide and hydrogen. The methanol synthesis process is not considered to be per se invented here. Various methanol synthesis processes are commercially available from different vendors which may operate similarly or differently. It is believed that any and all of these would be suitable for use in this invention. In general, these processes operate with a zinc-copper catalyst at about 350° to 650° F at about 700 to 2500 psig. Conversions in these processes are usually relatively low and so recycle ratios of about 4 to 10 to 1 are conventional.

At least the methanol, and preferably the entire organic oxygenate, portion of the product is then converted to water and an organic product comprising high octane hydrocarbon gasoline as a major constituent of the organic product. This methanol conversion process is carried out at about 500° to 1200° F and 0.5 to 50 LHSV at relatively low pressure conditions of slight vacuum up to about 600 psig using a special zeolite catalyst to be described below. The methanol conversion process can be carried out in one or a series of steps as desired to produce a product comprising water and a full range of hydrocarbons from $C_1$ to about $C_{10}$. The light, $C_4-$, hydrocarbons are normally gaseous and contain substantial quantities of isobutane and $C_3$ and $C_4$ olefins. The heavier, $C_5+$, hydrocarbons are normally liquid and boil in the normal gasoline boiling range. They have a high octane number up to about 110 and are highly aromatic in composition. The $C_5^+$ fraction represents the major fraction of the hydrocarbon portion of the product up to about 80% thereof in some cases.

In another embodiment of this invention, the synthesis gas is converted directly to water and a full range of hydrocarbons from $C_1$ to about $C_{10}$. The hydrocarbons so produced again divide into $C_4^-$ normally gaseous hydrocarbons and $C_5^+$ normally liquid high octane, aromatic gasoline. The light saturated hydrocarbons are more prevalent in this product than in the product produced via methanol as aforesaid, but there is a processing advantage of simplified, one step procedure to compensate. The $C_4^-$ fraction contains significant quantities of $C_3$ and $C_4$ olefins as well as isobutane. This one step conversion operates at about 300° to 800° F and 50 to 1500 psig. The catalyst is a mixture of carbon monoxide reduction catalyst, preferably one which is not too strong an olefin hydrogenation catalyst, and a special zeolite to be described below. The carbon monoxide reduction catalyst is illustrated by thorium, iron, cobalt, ruthenium and rhodium.

The product comprising hydrocarbon gasoline produced by either the direct or indirect (via methanol intermediate) process described above is suitably resolved into three phases: an aqueous phase, containing very little, if any, hydrocarbons, which is suitably recycled to the aforesaid steam reformer; a $C_5^+$ gasoline boiling range product which is suitably recovered; and a $C_4^-$ hydrocarbon gas phase. The $C_4^-$ phase product is divided into two fractions: a $C_2^-$ dry gas which also contains the hydrogen and carbon oxides which may be present and is recycled to the aforesaid steam reformer, suitably augmented by additional carbon dioxide as aforesaid, if desired; an alkylation feed fraction comprising the previously identified $C_3$ olefins, $C_4$ olefins and isobutane. This last fraction can be adjusted in relative proportions vis a vis each other by controlling the processing conditions in the gasoline producing step previously described, e.g., olefin content may be increased by increasing space velocity.

This alkylation feed fraction is suitably subjected to conventional acid catalyzed alkylation to produce high octane $C_7$ and $C_8$ alkylate which is admixed with the highly aromatic gasoline produced in the second step of this process. As noted, the alkylation process is not considered to be per se inventive here. Such processes are available from various commercial vendors utilizing sulfuric or hydrofluoric acid catalysts. They generally operate at temperatures up to about 450° F and at pressures up to about 500 psig.

The gasoline product produced by this integrated process has exceptional volatility and octane characteristics and requires no lead or other octane appreciators. In fact, under some circumstances, its octane values are substantially in excess of those required for the operation of modern motor vehicles. It may, therefore, be desirable to increase the volume of gasoline produced by this integrated process, and reduce the octane thereof to some extent, but not necessarily to less than that required for a modern lead free gasoline, by admixing substantial volumes of low octane gasoline boiling range fractions, such as natural gasoline, virgin naphtha, natural gas liquids, straight run naphtha or the like, therewith. It may be particularly desirable to conduct this entire integrated operation in proximity to a large natural gas field so that the liquids extracted therefrom can be blended right back into the gasoline product produced. Thus, except for thermal and other efficiency losses, substantially everything coming out of the gas well is converted to LPG and high quality gasoline, a most desirable consequence.

Since the light gas ($C_1$ and $C_2$) produced in the process is recycled to extinction to the reformer and since intermediate unconverted carbon oxides and hydrogen are recycled to extinction in the syn gas converter, and since the water coproduced with the gasoline in the zeolite catalyzed conversion is recycled to extinction in the steam reformer, substantially all of the fed natural gas is upgraded to fuel and more valuable LPG and gasoline products. Some carbon dioxide may be vented or added from time to time as needed and some water may be added or discharged from time to time as needed. In general, however, one of the principal advantages of this system is that recycled light gas and water, in addition to improving carbon and hydrogen efficiency, effectively act as heat sink, heat transfer materials with respect to removing the exothermic heat of reaction of this total process.

Referring now to the drawing for a detailed analysis of one embodiment of this invention:

As shown in FIG. 1, natural gas 12 is contacted with steam 10 in a conventionally operated steam reformer 14. The synthesis gas 16 thus formed, comprising carbon oxides and hydrogen, which may or may not have been adjusted in its ratio of carbon oxides to hydrogen, is then fed to a methanol synthesis reaction zone 18 where a portion of it is converted to methanol. The product 20 of methanol synthesis, from which unreacted synthesis gas has been purged and recycled 22, is fed into contact with a special zeolite 24 where it is converted to a mixture of water 26, and hydrocarbon 28. The water 26 is suitably removed and recycled to the steam reformer 14 while the hydrocarbon 28 is fed to a gas plant 38 where it is resolved into dry gas 40 ($C_1 + C_2$), which is recycled to the steam reformer or used as synthetic natural gas for process heat or otherwise, an alkylation feed fraction comprising $C_3$ and $C_4$ hydrocarbons and $C_5^+$ aromatic gasoline 30. This mixture 36 is fed to an alkylation unit 34 conventionally operated with a strong acid catalyst such as hydrofluoric acid. In the alkylation unit 34, olefins react with isoparaffins, particularly $C_3$ and $C_4$ olefins with isobutane, to produce alkylate 44, a high quality gasoline product which is suitably blended with the previously made aromatic gasoline 30.

Referring now to FIG. 2, natural gas 50 is contacted in a reformer 52 with steam 54 to produce a synthesis gas 56. This synthesis gas 56, after mixing with recycle stream 51, is converted in contact with a catalyst 60, comprising a carbon monoxide reduction catalyst and a special zeolite, to produce water 62, which is suitable recycled 64 to the reformer 52, and hydrocarbon 66. The hydrocarbon 66 is resolved in a gas plant 70 into $C_2^-$ tail gas 74 which is recycled, alkylation feed fraction 76 and $C_5^+$ aromatic gasoline 68. This latter fraction 76 is converted in an alkylation unit 78, using an acid catalyst 80, into $C_7$ and $C_8$ alkylate 82 which is mixed with the aromatic gasoline 68 previously produced to constitute very high quality gasoline 84. As a measure to adjust the carbon and hydrogen ratios as well as to conserve carbon in the system, $CO_2$ may be introduced from flue gas 86 or other sources 88 or released from the system as required.

The special zeolite catalysts referred to herein utilize members of a special class of zeolites exhibiting some unusual properties. These zeolites induce profound transformation of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in type B catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by eight-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° and 950° F to give an overall conversion between 10 and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The constraint index is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| TMA Offretite | 3.7 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property Constraint Index as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same idential zeolite tested under other defined conditions may give a constraint index value outside of 1 to 12.

The class of zeolites defined herein is exemplified by ZSM-5, ZSM-11, ZSM-12, ZMS-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. patent Application Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two different zeolites, one or both of which are the effective material insofar as the catalysis of this invention is concerned. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for 1 hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired, Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume, cc/cc | Framework Density, q/cc |
| --- | --- | --- |
| Ferrierite | 0.28 | 1.76 |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

According to this invention natural gas and steam and carbon dioxide if available, are reacted together in a mole proportion of about 0.20 to 0.67 to 1, at a temperature of about 1400° to 1800° F and a pressure of about 100 to 500 psig. A nickel catalyst may be employed. The synthesis gas product contains carbon oxides, hydrogen and may contain water as well. Mole ratios of hydrogen to carbon monoxide are suitable about 1 to 5 to 1. Carbon dioxide is suitable in a mole ratio of about 0.25 to 1.00 to 1 to the carbon monoxide present.

Methanol synthesis is generally carried out at about 350° to 650° F and 700 to 2500 psig at a conversion of about 90 to 98 percent (thus a recycle ratio of about 4 to 10 to 1). A copper-zinc catalyst which may also contain chromium, all in the oxide form is usually used.

The special zeolite conversion is suitable operated at about 500° to 1200° F, preferably about 600° to 800° F, and about 0.5 to 50 LHSV. It is suitably a fixed bed, downflow reaction zone but it may be operated as a fluidized or transport bed and/or upflow reactor. The reaction product is cooled to an extent sufficient to condense the water and the $C_5+$ hydrocarbons. Thus, the product is separated into three phases, a light hydrocarbon gas, a heavier hydrocarbon liquid and an aqueous liquid.

The alkylation unit preferably uses a homogeneous catalyst such as sulfuric or hydrofluoric acids and operates at about 0° to 450° F and 0 to 500 psig.

What is claimed is:

1. A process comprising:
reforming natural gas with steam to a synthesis gas product comprising hydrogen and carbon monoxide in ratio of about 1 to 5 to 1;
converting said synthesis gas product to a product comprising water, $C_4-$ light hydrocarbon gas and $C_5+$ gasoline boiling range hydrocarbons containing monocyclic aromatics utilizing at least one catalyst comprising a crystalline aluminosilicate zeolite having a silica to alumina ratio of at least 12 and a constraint index of 1 to 12;
separating the hydrocarbon portion of said conversion product into water, $C_4-$ hydrocarbon gas and $C_5+$ gasoline;
separating said $C_4-$ gas into $C_2-$ tail gas, and on alkylation feed fraction comprising saturated and unsaturated $C_3$ and $C_4$ hydrocarbons;
recycling said tail gas to said steam reforming;
reacting said alkylation feed fraction in contact with an acid catalyst to gasoline boiling range aliphatic products comprising $C_7$ and $C_8$ alkylate; and
admixing said alkylate gasoline and said aromatic gasoline.

2. The process claimed in claim 1 including converting said synthesis gas to an organic product comprising methanol by contact with a catalyst comprising zinc and copper; and converting said methanol to said water and hydrocarbons by contact with a catalyst comprising said zeolite.

3. The process claimed in claim 1 including converting said synthesis gas directly to said aromatic gasoline by contacting such with a catalyst comprising as a first component said zeolite and as a second component a metal value having strong carbon monoxide reducing catalytic activity and weak olefin hydrogenation catalytic activity.

4. The process claimed in claim 2 including reforming at about 1400° to 1800° F and 100 to 500 psig, synthesizing methanol at about 350° to 650° F and about 700 to 2500 psig, aromatizing methanol at about 500° to 1200° F and 0.5 to 50 LHSV, and alkylating at up to about 450° F and up to about 500 psig.

5. The process claimed in claim 3 including converting said synthesis gas at about 300° to 800° F and 50 to 1500 psig.

6. The process claimed in claim 3 wherein said second catalyst component is at least one metal selected from the group consisting of thorium, iron, ruthenium rhodium and cobalt.

7. The process claimed in claim 1 wherein said special zeolite is a ZSM-5 zeolite.

8. The process claimed in claim 6 including providing a basic metal with said second catalyst component.

9. The process claimed in claim 8 wherein said basic metal is potassium.

10. The process claimed in claim 1 including separating natural gas liquids from said natural gas prior to said reforming, and admixing said natural gas liquids with said mixed aromatic and alkylate gasoline.

* * * * *